(12) United States Patent
Bruce et al.

(10) Patent No.: US 6,387,411 B2
(45) Date of Patent: *May 14, 2002

(54) METHOD FOR PRODUCING DISPERSIBLE STEROL AND STANOL COMPOUNDS

(75) Inventors: Richard D. Bruce, Rydal; Brid Burruano, King of Prussia; Michael R. Hoy, Sellersville, all of PA (US); Nicholas R. Paquette, Danbury, CT (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/826,072

(22) Filed: Apr. 4, 2001

Related U.S. Application Data

(62) Division of application No. 09/200,623, filed on Nov. 30, 1998, now Pat. No. 6,242,001.

(51) Int. Cl.$^7$ .............................. A61K 9/14; A61K 9/20
(52) U.S. Cl. ...................... 424/489; 424/464; 424/465; 514/772.3; 514/772.4; 514/784; 514/785; 514/786; 514/951
(58) Field of Search ................................ 424/451, 464, 424/465, 489, 484, 486, 455

(56) References Cited

U.S. PATENT DOCUMENTS

| 3,004,043 A | 10/1961 | Stern |
| 3,085,939 A | 4/1963 | Wruble et al. |
| 3,865,939 A | 2/1975 | Jandacek |
| 3,881,005 A | 4/1975 | Thakkar et al. |
| 4,005,196 A | 1/1977 | Jandacek et al. |
| 4,195,084 A | 3/1980 | Ong |
| 4,391,732 A | * 7/1983 | Lundmark .................. 252/356 |
| 4,423,041 A | 12/1983 | Clum et al. |
| 5,219,733 A | 6/1993 | Myojo et al. |
| 5,244,887 A | 9/1993 | Straub |
| 5,270,041 A | 12/1993 | Eugster et al. |

(List continued on next page.)

FOREIGN PATENT DOCUMENTS

| EP | 0053415 B1 | 6/1982 |
| EP | 0057075 B1 | 8/1982 |
| EP | 0719583 A1 | 4/1986 |
| EP | 0289636 A1 | 11/1988 |
| EP | 0357967 A1 | 3/1990 |
| EP | 0357967 B1 | 3/1990 |
| GB | 1284814 | 8/1972 |
| WO | WO 92/19640 A1 | 11/1992 |
| WO | WO 96/10033 A1 | 4/1996 |
| WO | WO 96/38047 A! | 12/1996 |
| WO | WO 98/06714 A1 | 2/1998 |
| WO | WO 99/18977 A1 | 4/1999 |
| WO | WO 99/56729 A1 | 11/1999 |
| WO | WO 99/63841 A1 | 12/1999 |

OTHER PUBLICATIONS

Database WPI Week 9507 Derwent Publications Ltd., London GB;AN 1995–048788 XP002133284 JP 06 329588A (Riken Vitamin Co.) Nov. 29, 1994 Abstract.

T. Heinemann et al. "Mechanisms of Action of Plant Sterols on Inhibition of Cholesterol Absorption:". Eur J. Clin Pharmacol (1991) 40 [Suppl 1]: pp. 559–563.

United States Pharmacopeia, 23rd Edition, Section 851, pp. 1832 and 1835.

USSN 09/145,528, filed Sep. 2, 1998. Status: Pending "Sterol Esters in Tableted Solid Dosage Forms".

*Primary Examiner*—James M. Spear

(57) ABSTRACT

A method for preparing sterol/stanol and sterol/stanol ester compositions with improved dispersibility is provided by co-melting the sterol/stanol and/or sterol/stanol ester with highly branched hydrocarbons and then grinding the resulting product. A method for preparing the compounds is also disclosed. The ground compound is suitable for formulating into orally administered products suitable for control of blood serum cholesterol.

10 Claims, 1 Drawing Sheet

U.S. PATENT DOCUMENTS

| | | |
|---|---|---|
| 5,492,714 A | 2/1996 | Guskey et al. |
| 5,502,045 A | 3/1996 | Miettinen et al. |
| 5,578,334 A | 11/1996 | Sundram et al. |
| 5,629,316 A | 5/1997 | Kurihara et al. |
| 5,698,527 A | 12/1997 | Kim |
| 5,723,747 A | 3/1998 | Lassner et al. |
| 5,837,714 A | 11/1998 | Rocco et al. |
| 5,932,562 A | 8/1999 | Ostlund, Jr. |
| 6,025,010 A | 2/2000 | Reddy |
| 6,025,348 A | 2/2000 | Goto et al. |
| 6,031,118 A | 2/2000 | van Amerongen et al. |
| 6,045,853 A | 4/2000 | Reddy |
| 6,054,144 A | 4/2000 | Burruano et al. |
| 6,110,502 A | 8/2000 | Burruano et al. |
| 6,242,001 B1 * | 6/2001 | Bruce et al. ............ 424/464 |

* cited by examiner

METHOD FOR PRODUCING DISPERSIBLE STEROL AND STANOL COMPOUNDS

RELATED APPLICATIONS

This application is a divisional of U.S. patent application Ser. No. 09/200,623, filed on Nov. 30, 1998, now U.S. Pat. No. 6,242,001B1.

FIELD OF THE INVENTION

The present invention relates to a method of producing sterols/stanols, in particular a method for producing β-sitosterol, with improved wetting and dispersion properties.

BACKGROUND OF THE INVENTION

As disclosed in U.S. Pat. Nos. 5,244,877, 5,502,045 and 5,578,334, various sterols/stanols, in particular β-sitosterol, are known to have cholesterol-lowering properties. The consumption of β-sitosterol is known to reduce cholesterol levels in the blood stream. Presently due to its handling and storage properties, β-sitosterol is incorporated in foods during its formulation, or while it is being manufactured. While this is effective in producing foods with beneficial effects, the consumer is limited to those foods in which the manufacturers incorporate β-sitosterol.

It would be highly desirable to provide sterols/stanols in a form that would be readily dispersible in aqueous media, thus increasing the amount available to micelles in the gut.

There have been several attempts to provide such a product with limited success. U.S. Pat. No. 3,881,005 discloses the use of a polyoxyethlene sorbitan monostearate that is added to a sterol suspension prior to spray drying. U.S. Pat. No. 4,195,084 discloses a tall oil suspension suitable for oral administration that is comprised of finely divided particles of β-sitosterol in water. Other solutions described in the art include, U.S. Pat. No. 3,004,043 which discloses water-soluble vegetable oil sterol derivatives and U.S. Pat. No. 3,085,939 which discloses oil-in water sterol emulsions. While these disclosures provide edible compositions of sterols, the disclosures fail to provide the sterol in a form that would be more readily available to the body.

FIELD OF THE INVENTION

A primary object of the present invention is to provide orally administered self-dispersing solid compositions and methods of producing these compositions that contain sterols/stanols and hydrocarbons for control of blood serum cholesterol. An orally administered sterols/stanols and highly branched hydrocarbon solid dosage form is also claimed. These compositions are provided without the intentional addition of water to the composition.

DETAILED DESCRIPTION OF THE INVENTION

Figure 1:
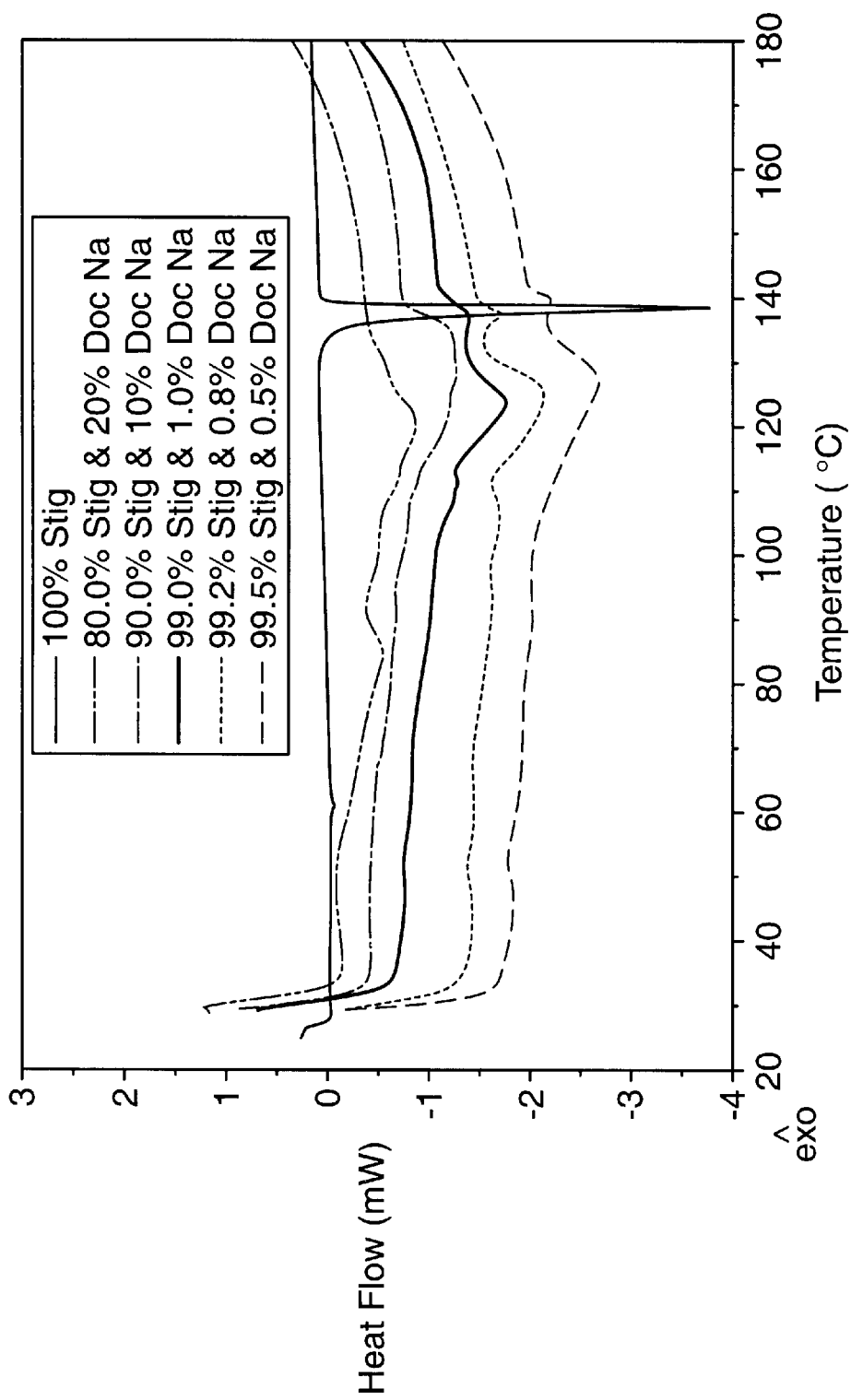
FIG. 1 is a plot of melting point of various β-sitosterol/ docusate sodium matrices.

Sterols/stanols are typically derived from agricultural sources, such as corn, soy-based, and pine tree mixtures, and as such are commonly referred to as sterols. The present invention also contemplates esters of sterols/stanols through the reaction of the stanol/sterol with the suitable acid. Suitable acids include saturated, unsaturated and polyunsaturated acids Suitable acids include but not limited to stearic, butyric, lauric, palmitic, oleic, linoleic, linolenic, docohexanoic acid and the like. Suitable methods for preparing these esters are well known in the art, see for example, U.S. Pat. Nos. 5,502,045, 5,723,747, the contents of which are incorporated herein by reference. The present invention also includes stanols, the reduction product of sterol and hydrogen, this reaction is well known to those with skill in the art.

The present invention also employs a food grade acceptable hydrocarbon, preferably a branched hydrocarbon. As used throughout this specification, food grade acceptable is defined as a material that is appropriate to be incorporated into and consumed in a food by humans. The present invention also includes food grade acceptable salts of these compounds.

As used throughout this invention the hydrocarbon disrupters are understood to be a compound which contains primarily carbon and hydrogen atoms and preferably contains at least 3 branched units in the compound. Other atoms including but not limited to oxygen, nitrogen and sulfur may also be included in the highly branched hydrocarbon. As used in this specification, branched is understood to mean a hydrocarbon chain having a length of at least two carbon atoms, preferably three or more and more preferably 4 or more carbon atoms in length that are pendent from the major backbone of the molecule.

Among the highly branched hydrocarbons suitable for use in the invention include docusate sodium; blends of polyglycolized glycerides consisting of mono-, di, and tri glycerides and of mono-, and di-fatty esters of polyethylene glycol commercially available as Gelucire 44/14; Gelucire 50/13 (both from Gattefosse Corp.); acetylated monoglycerides, commercially available as Myvacet 600 (Eastman Fine Chemicals); polyoxyl 40 hydrogenated caster oil commercially available as Cremopor RH40 (BASF Corp.); polyoxyethylene 20 sorbitan monopalmitate available commercially as TWEEN 40; and SPAN 80 (both from ICI Chemicals & Polymers of America).

Linear polymeric materials, such as polyethylene glycol, ,polyoxyethylene, polyoxypropylene or poloxamer, a non-ionic polyoxyethylene -polyoxypropylene co-polymer commercially available from BASF Corp., while not branched also produce the disruption effect due to the variations in chain length present in these materials.

The hydrocarbon is typically incorporated as a solid at a level of from about 0.1 to about 50; preferably from about 0.4 to about 10; and most preferably from about 0.5 to about 0.8 weight percent in the solid.

The hydrocarbon is added to the sterols/stanols typically by co-melting the materials to a single-phase molten solution result. It is then preferable to cool and grind the resulting mixture so as to have a more easily handled particle size. Typical particle sizes are from about 10 to about 150 microns, preferably from about 25 to about 75 microns. Suitable methods include pulverizing, rotary hammermill, air milling and the like of which air milling is most preferred. Smaller particles sizes are preferred in that the resulting β-sitosterol product is more readily exposed to bile salts in the digestive tract.

A preferred method of determining whether the proper level of hydrocarbon has been added to the sterol is to employ differential scanning calorimetry (DSC). This technique measures the heat flow in the sample as a function of temperature. The incorporation of the highly branched hydrocarbon in the sterols/stanols reduces the crystallinity of the solid, which results in improved water dispersibility. When using DSC, sufficient crystal lattice disruption is known when the heat of fusion of the sterol/phytostanol peak drops to less than about 2, and more preferably less than about 1 Joule/gram, signifying a significant loss of crystal lattice energy. It is this low lattice energy which causes a huge increase in wetting ability of sterol/stanol comelts with lattice-disrupting materials claimed in this invention.

Another technique for measuring the crystallinity of the solid matrix is to measure the time in which a ground powdered sample of the solid takes to disperse in unstirred water. When an appropriate amount of the appropriate hydrocarbon material has been added, the solid solution will disperse in fifty milliliters of water in less than about 60 seconds, preferably in less than about 45 seconds and most preferably less than about 30 seconds. Agitation, including mild agitation such as a stirring bar, can be employed to enhance the dissolution of the solid solution in water.

Yet another method to determine whether the desired level of hydrocarbon has been added to the sterol/stanol, is to measure the turbidity of the solution after 100 milligrams of the ground sterol/stanol/hydrocarbon are added to water. The greater turbidity value, the more effectively the solid solution is able to be dispersed in water. Mixtures of sterol/stanol and hydrocarbon with higher turbidty values are believed to provide a more effective in reducing cholesterol when consumed. Preferred turbidity levels are greater than about 1500, preferably greater than 2000 and most preferably greater than 3000 Nephelometric Turbidity Units (NTU). As used herein turbidity is understood to be the same as defined by the *United States Pharmacopeia*, 15$^{th}$ Edition, the light scattering effect of suspended particles and turbidity as the measure of the decrease in the incident beam intensity per unit length of a given suspension. The range of turbidty values is from 0 to 20,000 NTU. As a point of reference the turbidity of water is zero. The turbidity of the samples is measured at room temperature.

Prior to the present invention, sterols were administered as a poorly soluble crystalline solid. The present invention makes possible the solid solution delivery of invention for treatment of hypercholesterolemia. The present invention includes embodiments of oral solid dosage forms as capsules, including semi-solid fills of the present invention in soft capsules or hard-shell gelatin capsules; melt or extruded molded solid tablets; and directly compressed tablets made from blends of the sitosterol mixtures with standard tableting excipients. In addition, the present invention can be included as semi-solid mixtures for inclusion in foodstuffs. As used in this invention, semi-solid is understood to mean highly viscous materials that do not flow easily. Generally semi-solid materials have a viscosity of greater than about 5,000 centipoise, more typically greater than about 10,000 centipoise.

A principal advantage of the present invention is the production of sterol/stanol with improved dispersibility that minimizes the incorporation of additional ingredients, i.e. surfactants, dispersants, etc. Furthermore, since the hydrocarbon is added to the sterol/stanol as a solid, and without the addition of water to form an emulsion, suspension and the like, an expensive drying step is not required.

The present invention can also incorporate additional ingredients commonly used for making a tablet. Among these items are excipients which is understood to mean substance and materials used in the drug or food industry which do not alter the character and function of the active components of the aggregate. Flavors which may be optionally added are well known to those in the art, including synthetic flavor oils, and/or oils from plants, leaves flowers, fruits and so forth, and combinations thereof. Representative flavor oils include spearmint, peppermint, cinnamon, wintergreen, citrus oils, and fruit oils. Other suitable flavors include caramel, bubble gum and the like. Flavorings are typically employed at levels of from about 1 to about 5 weight percent.

Sweetening agents may also be employed such as monosaccharides, disaccharides, and polysaccharides such as xylose, ribose, glucose, mannose, galactose, fructose, dextrose, sucrose, maltose, corn syrup and the like. Artificial agents may also be employed including saccharin, cyclamates and acesulfam-K, aspartame, and the like. Sweeteners are typically employed at levels of from about 1 to about 5 weight percent.

Dispersal agents include hydroxymethyl cellulose, corn starch, croscarmellose cellulose (Ac-Di-Sol made by FMC Corp.) and mixtures thereof. Dispersal agents may be incorporated from about 2 to about 20 weight percent.

Lubricants can also be added to the mixture to aid in the processing of the tablets. These compounds are well known in the art, with magnesium stearate being most preferred. Lubricants are typically employed at levels of from about 1 to about 5 weight percent.

After the invention is ground to a powder it is packaged in any suitable size as may be required. The form the invention is contained in may also vary depending on the preference of the consumer. Suitable forms include tablets, chewable dosages or applied to beverages and foodstuffs. In a preferred embodiment, the invention may be packaged in single serving size packets containing from about 5 to about 50 grams per packet.

The invention will now be illustrated by, but is not intended to be limited to, the following examples. In these examples it is understood that unless noted otherwise, all parts are weight percent.

EXAMPLE 1

Sterols (Generol 122 available from Henkel Corp.) and 20% docusate sodium U.S.P. were melted at 150° C. The mixture was cooled to ambient temperature, approximately 23° C. and first coarsely chopped then milled under liquid nitrogen to a powder of approximately 40 micron mean diameter.

EXAMPLE 2

The powder of Example 1 was added to approximately 50 milliliters of water and was found to spontaneously wet and disperse without stirring.

EXAMPLE 3

A docusate sodium/β-sitosterol matrix was prepared. The sample was shaken for 30 seconds in a vial containing 25 milliliter deionized water. In Series 1, turbidity measurements were taken after allowing the shaken sample to stand one minute. In Series 2, measurements were made after standing for 20 minutes. The results are provided in the following table.

| % Docusate sodium | Series 1 (NTU) | Series 2 (NTU) |
| --- | --- | --- |
| 10 (1st batch) | 600 | 386 |
| 10 (2nd batch) | 538 | 231 |
| 1 | 921 | 700 |
| 0.8 | 2136 | 1777 |
| 0.5 | 1841 | 1573 |
| 0.1 | 714 | 307 |
| 100% sterol | 1301 | 523 |
| 100% docusate sodium | 1.22 | 0.441 |
| Deionized water | 0.85 | 0.6 |

The 100% sterol, 100% docusate sodium and water were employed as controls. This example demonstrates an optimal range of about 0.5 to about 0.8 weight percent sodium docusate incorporated in the sterol material for purposes of providing a dispersible sterol material.

EXAMPLE 4

A 500 milligram sample of a 99:1 sitosterol/docusate sodium matrix was placed in 200 milliliters of unstirred tap water at ambient temperature resulted in the sample dispersing into the water in 25 seconds.

EXAMPLE 5

Additional sitosterol/docusate sodium matrices were prepared and added to water. The mixtures demonstrated enhanced wetting as reported in the table below.

| Percent docusate sodium In Matrix | Time (seconds) to disperse 200 mg of Sample in 250 ml Unstirred Water |
| --- | --- |
| 20 | 97 |
| 10 | 8 |
| 1.0 | 7 |
| 0.8 | 11 |
| 0.5 | 45 |

By comparison, a 100% sitosterol powder sample under similar conditions does not wet at all, samples left for a long as three days with vigorous stirring immediately floated to the top of the water when agitation was stopped.

The above results depict a range of docusate sodium which provides a range of values with high degree of dispersibility in water.

EXAMPLE 6

Docusate sodium was used as the lattice disrupting material and was co-melted and recongealed with β-sitosterol. Differential scanning calorimetry (DSC) was used to measure the heat flow as a function of temperature. The results are provided in FIG. 1. As measured using DSC sufficient disruption of the crystal lattice occurs when the heat of fusion of the β-sitosterol peak drop to less than about 1 Joule/gram.

What is claimed is:

1. A solid composition suitable to be orally administered comprising a sterol/stanol or sterol/stanol ester composition in an amount sufficient to lower serum cholesterol and an effective amount of a hydrocarbon selected from the group consisting of docusate sodium; mono, di and tri glycerides, polyglycolized glycerides, mono-, and di-fatty esters of polyethylene; acetylated monoglycerides; polyoxyl 40 hydrogenated castor oil; and polyoxyethylene 20 sorbitan monopalmitate to provide a water dispersible mixture, wherein the composition is prepared without the intentional addition of water.

2. A method of producing a water-dispersible dosage form to be orally administered containing a sterol/stanol or sterol/stanol ester comprising:

a) providing a sterol/stanol or sterol/stanol ester in an amount sufficient to reduce serum cholesterol;

b) providing a hydrocarbon selected from the group consisting of docusate sodium; mono, di and tri glycerides, polyglycolized glycerides, mono-, and di-fatty esters of polyethylene; acetylated monoglycerides; polyoxyl 40 hydrogenated castor oil; and polyoxyethylene 20 sorbitan monopalmitate, polyethylene glycol, polyoxyethylene, polyoxypropylene, and polyoxyethylene/polyoxypropylene co-polymers in an amount sufficient to provide a water dispersible form;

c) admixing the sterol/stanol or sterol/stanol ester and the hydrocarbon in the absence of water; and d) grinding the mixture to a particle size of from about 25 to about 75 microns.

3. A solid composition suitable to be orally administered comprising:

a sterol/stanol or sterol/stanol ester composition in an amount sufficient to lower serum cholesterol and from about 0.4 to about 10 weight percent polyoxyethylene 20 sorbitan monopalmitate; thereby providing a water dispersible mixture, the solid composition free of water.

4. A composition of claim 3, wherein the sterol/stanol or sterol/stanol ester is present in an amount of from about 50 to about 99.9 weight percent.

5. A composition of claim 3, wherein the amount of polyoxyethylene 20 sorbitan monopalmitate is from about 0.5 to about 0.8 weight percent.

6. A composition of claim 4, wherein the amount of polyoxyethylene 20 sorbitan monopalmitate is from about 0.5 to about 0.8 weight percent.

7. A method for producing a water-dispersible dosage form to be orally administered containing a sterol/stanol or sterol/stanol ester comprising:

a) providing a sterol/stanol or sterol/stanol ester in an amount sufficient to reduce serum cholesterol;

b) providing from about 0.4 to about 10 weight percent polyoxyethylene 20 sorbitan monopalmitate c) admixing the sterol/stanol or sterol/stanol ester and the hydrocarbon in the absence of water to provide a water dispersible form.

8. A method of claim 7, wherein the sterol/stanol or sterol/stanol ester is present in an amount of from about 50 to about 99.9 weight percent.

9. A method of claim 7, wherein the amount of polyoxyethylene 20 sorbitan monopalmitate is from about 0.5 to about 0.8 weight percent.

10. A method of claim 8, wherein the amount of polyoxyethylene 20 sorbitan monopalmitate is from about 0.5 to about 0.8 weight percent.

* * * * *